United States Patent
Alam et al.

(10) Patent No.: US 10,125,371 B2
(45) Date of Patent: Nov. 13, 2018

(54) **NUCLEOTIDE SEQUENCE ENCODING WUSCHEL-RELATED HOMEOBOX4 (WOX4) PROTEIN FROM *CORCHORUS OLITORIUS* AND *CORCHORUS CAPSULARIS* AND METHODS OF USE FOR SAME**

(71) Applicants: BANGLADESH JUTE RESEARCH INSTITUTE, Dacca (BD); Rafia Hasina, Honolulu, HI (US)

(72) Inventors: Maqsudul Alam, Honolulu, HI (US); Mohammed Shahidul Islam, Dacca (BD); Borhan Ahmed, Dacca (BD); Mohammed Samiul Haque, Dacca (BD); Mohammed Monjurual Alam, Dacca (BD)

(73) Assignee: Bangladesh Jute Research Institute, Dhaka (BD)

( * ) Notice: Subject to any disclaimer, the term of this patent is extended or adjusted under 35 U.S.C. 154(b) by 24 days.

(21) Appl. No.: 14/781,169

(22) PCT Filed: Nov. 20, 2014

(86) PCT No.: PCT/US2014/066599
§ 371 (c)(1),
(2) Date: Sep. 29, 2015

(87) PCT Pub. No.: WO2015/077447
PCT Pub. Date: May 28, 2015

(65) Prior Publication Data
US 2016/0369288 A1 Dec. 22, 2016

Related U.S. Application Data

(60) Provisional application No. 61/907,617, filed on Nov. 22, 2013.

(51) Int. Cl.
*C12N 15/82* (2006.01)
*C07K 14/415* (2006.01)
*A01H 5/00* (2018.01)

(52) U.S. Cl.
CPC ........ *C12N 15/8242* (2013.01); *C07K 14/415* (2013.01); *C12N 15/8218* (2013.01); *C12N 15/8246* (2013.01); *C12N 15/8261* (2013.01)

(58) Field of Classification Search
CPC ............ C12N 15/8261; C12N 15/8242; C07K 14/415
See application file for complete search history.

(56) References Cited

U.S. PATENT DOCUMENTS

2011/0004958 A1 1/2011 Aloni et al.
2011/0283420 A1* 11/2011 Hatzfeld .............. C07K 14/415
800/290

FOREIGN PATENT DOCUMENTS

WO WO-2010/086221 A1 8/2010

OTHER PUBLICATIONS

Guo et al (PNAS 2004 (101)25, 9205-9210) (Year: 2004).*
Ikeda et al (The Plant Cell Nov. 2009, 21 (11) 3493-3505) (Year: 2009).*
Gorshkova, T. et al., "Plant Fiber Formation: State of the Art, Recent and Expected Progress, and Open Questions," Critical Reviews in Plant Sciences, 31:201-228 (2012).
Ji, Jiabing, et al., "WOX4 Promotes Procambial Development[W][OA]," Plant Physiology, 152:1346-1356 (2010).
Ohmori, Y. et al., "WUSCHEL-Related Homeobox4 Is Involved in Meristem Maintenance and is Negatively Regulated by the CLE Gene FCP1 in Rice," The Plant Cell, 25:229-241 (2013).
"Populus x canadensis WUSCHEL-related homeobox 4 (W0X4) mRNA, complete cds.", retrieved from EBI accession No. EM-STD:KC691250; (Jun. 4, 2013).
"Subname: Full=WUSCHEL-related homeobox 4 {ECO:0000313 | EMBL:AGM48535.1};". retrieved from EBI accession No. UNIPROT:R9RIF3 (Sep. 18, 2013).
Zheng, J. et al., "Transcriptional Analysis Provides New Insights into Cold- and Dehydration-Tolerance Signaling Pathways and on Regulation of Stem Cell Activity in the Vascular Cambium of Poplar," Plant Mol. Biol. Rep, 31:75-86 (2013).
Supplementary European Search Report dated Nov. 23, 2015 for EP 14 85 9333.

* cited by examiner

Primary Examiner — Lee A Visone
(74) Attorney, Agent, or Firm — Foley Hoag LLP; Dana M. Gordon; Thi K. Do (57) ABSTRACT

The present invention discloses isolated polynucleotides encoding WUSCHEL-related homeobox4 proteins from two species of jute plants, namely, the *Corchorus olitorius* ("*C. olitorius*") and *Corchorus capsularis* ("*C. capsularis*"), and corresponding polypeptides derived therefrom. The disclosed polynucleotide sequences encode WUSCHEL-related homeobox4 polypeptides (WOX4), which possess catalytic activities in enhancing fiber production in jute. The present invention also relates to the plants having a modulated expression of a nucleic acid encoding a WOX4 polypeptide, which have enhanced fiber yield relative to corresponding wild type plants or other control plants. Vectors, expression constructs and host cells comprising and/or consisting of the nucleotide sequences of the protein are also provided. Also disclosed are methods for producing the proteins and methods for modifying the proteins in order to improve their desirable characteristics. The proteins of the invention can be used in a variety of ways, including inducing, initiating, improving, or enhancing plant growth, plant height, fiber and seed yield.

13 Claims, 1 Drawing Sheet
Specification includes a Sequence Listing.

SEQUENCE LISTING

<160> NUMBER OF SEQ ID NOS: 12

<210> SEQ ID NO 1
<211> LENGTH: 1250
<212> TYPE: DNA
<213> ORGANISM: Corchorus olitorius

<400> SEQUENCE: 1

| | | | | | |
|---|---|---|---|---|---|
| acctcatcat | ttggtcttgg | ttcttcaaag | caccacctca | tatcccactt | tcttttcctt | 60 |
| ttcttttttt | taaaatttt | atttttggg | ttaaatttat | ttttgttatt | atataatcag | 120 |
| agcattctcc | ccatcattca | ctccttcacc | atgggaaaca | tgaaggtgca | tcagttggca | 180 |
| cgtggcttat | gggagcatga | accctccctc | tcccttggtt | gcaagcgctt | acgccctctt | 240 |
| gctcccaagc | tccacccttc | ctcttcccct | gatcatactt | ccgtctcctc | tttcgacctt | 300 |
| aagaccttca | ttcgtcccga | aagtggcccc | cgaaaacttt | gcccttctga | cgacaagcga | 360 |
| gattctcatt | ctccccaggt | acttacaaat | atccatgaaa | tgaaacccct | ttattttcc | 420 |
| aatgatgtat | ataattagtg | gggaaggata | agattttgaa | cttacgatga | acaataacag | 480 |
| tgtggaaagt | tgataatcaa | aggttaagaa | tgtgaagctg | aaactttttt | cttttttttg | 540 |
| gttatgtagg | tggaaacgca | cccaggggga | acgcggtgga | atccgacgca | agagcagata | 600 |
| gggatattgg | agatgctgta | tagaggtggg | atgcgaactc | caaatgcaca | gcaaatagaa | 660 |
| cagatcactg | cacagttagg | caagtacggg | aagatcgaag | gcaaaaacgt | tttctattgg | 720 |
| ttccaaaacc | acaaagcacg | cgaaaggcaa | agcagaagc | gtaacagtct | tggtcttagc | 780 |
| cattctccca | gaaactctgc | tcccattacc | accataactt | tggactctag | ggtaagttca | 840 |
| aaccaacaaa | acccttctt | tgtatatata | taacggttag | tttttagttt | ttacttctta | 900 |
| taaacagcaa | ttaacattaa | tgttttgtt | tatatatata | gggggaagta | atggagagag | 960 |
| aggaggatag | tccatataag | agaaagtgta | ggagctggtc | atttgagtac | ttagaagaag | 1020 |
| aaagcagatc | atcatcgtcg | agtcaagagg | aggaaaacag | aactctggag | cttttcccat | 1080 |
| tgcacccgga | aggcagatga | tggacgtttc | aactttgaaa | aacaaggaaa | aagggaagct | 1140 |
| taacccaaaa | ccaaaaagac | tgctacaaaa | cccaaaactc | tgttcccatt | tatgaaatga | 1200 |
| taaacatatg | ctttgatgat | ccatgatgat | gatgatgata | atgaagctga | | 1250 |

<210> SEQ ID NO 2
<211> LENGTH: 669
<212> TYPE: DNA
<213> ORGANISM: Corchorus olitorius

<400> SEQUENCE: 2

| | | | | | |
|---|---|---|---|---|---|
| atgggaaaca | tgaaggtgca | tcagttggca | cgtggcttat | gggagcatga | accctccctc | 60 |
| tcccttggtt | gcaagcgctt | acgccctctt | gctcccaagc | tccacccttc | ctcttcccct | 120 |
| gatcatactt | ccgtctcctc | tttcgacctt | aagaccttca | ttcgtcccga | aagtggcccc | 180 |
| cgaaaacttt | gcccttctga | cgacaagcga | gattctcatt | ctccccaggt | ggaaacgcac | 240 |
| ccaggggggaa | cgcggtggaa | tccgacgcaa | gagcagatag | ggatattgga | gatgctgtat | 300 |
| agaggtggga | tgcgaactcc | aaatgcacag | caaatagaac | agatcactgc | acagttaggc | 360 |
| aagtacggga | agatcgaagg | caaaaacgtt | ttctattggt | tccaaaacca | caaagcacgc | 420 |
| gaaaggcaaa | agcagaagcg | taacagtctt | ggtcttagcc | attctcccag | aaactctgct | 480 |
| cccattacca | ccataacttt | ggactctagg | ggggaagtaa | tggagagaga | ggaggatagt | 540 |
| ccatataaga | gaaagtgtag | gagctggtca | tttgagtact | agaagaaga | aagcagatca | 600 |

```
tcatcgtcga gtcaagagga ggaaaacaga actctggagc ttttcccatt gcacccggaa    660
ggcagatga                                                            669
```

<210> SEQ ID NO 3
<211> LENGTH: 222
<212> TYPE: PRT
<213> ORGANISM: Corchorus olitorius

<400> SEQUENCE: 3

```
Met Gly Asn Met Lys Val His Gln Leu Ala Arg Gly Leu Trp Glu His
1               5                   10                  15

Glu Pro Ser Leu Ser Leu Gly Cys Lys Arg Leu Arg Pro Leu Ala Pro
            20                  25                  30

Lys Leu His Pro Ser Ser Ser Pro Asp His Thr Ser Val Ser Ser Phe
        35                  40                  45

Asp Leu Lys Thr Phe Ile Arg Pro Glu Ser Gly Pro Arg Lys Leu Cys
    50                  55                  60

Pro Ser Asp Asp Lys Arg Asp Ser His Ser Pro Gln Val Glu Thr His
65                  70                  75                  80

Pro Gly Gly Thr Arg Trp Asn Pro Thr Gln Glu Gln Ile Gly Ile Leu
                85                  90                  95

Glu Met Leu Tyr Arg Gly Gly Met Arg Thr Pro Asn Ala Gln Gln Ile
            100                 105                 110

Glu Gln Ile Thr Ala Gln Leu Gly Lys Tyr Gly Lys Ile Glu Gly Lys
        115                 120                 125

Asn Val Phe Tyr Trp Phe Gln Asn His Lys Ala Arg Glu Arg Gln Lys
    130                 135                 140

Gln Lys Arg Asn Ser Leu Gly Leu Ser His Ser Pro Arg Asn Ser Ala
145                 150                 155                 160

Pro Ile Thr Thr Ile Thr Leu Asp Ser Arg Gly Glu Val Met Glu Arg
                165                 170                 175

Glu Glu Asp Ser Pro Tyr Lys Arg Lys Cys Arg Ser Trp Ser Phe Glu
            180                 185                 190

Tyr Leu Glu Glu Glu Ser Arg Ser Ser Ser Ser Gln Gly Glu Glu
        195                 200                 205

Asn Arg Thr Leu Glu Leu Phe Pro Leu His Pro Glu Gly Arg
    210                 215                 220
```

<210> SEQ ID NO 4
<211> LENGTH: 1237
<212> TYPE: DNA
<213> ORGANISM: Corchorus capsularis

<400> SEQUENCE: 4

```
tcacaagtca acctcacctc atcatttggt cttggttctt caaagcacca cctcatatcc     60
cacttccttt ttcaattttt aattttttt ggggttaaat ttatttggtt atataatcag    120
agcattctcc ccatcattca ctccttcacc atgggaaaca tgaaggtgca tcagttggca    180
cgtggcttat gggagcatga accctccctc tcccttggtt gcaagcgctt acgccctctt    240
gctcccaagc tccaccctt ctcttcccct gatcatactt ccgtctcctc tttcgacctt    300
aagaccttca ttcgtcccga agtggccccc ggaaactttt gcccttctga cgacaagcga    360
gattctcatt ctcgccaggt acttaaaaat taatatccat gaataatttt gtggggaagg    420
ataagttttg aacttaatgc ataataacag tgtggaaact taataggtta agaatatttg    480
```

| | | |
|---|---|---|
| aagaacttct atatatatga agctgaaact tttttgtggt gttgtaggtg gaaacgcacc | 540 |
| caggggga ac gcggtggaat ccgacgcaag agcagatagg gatactggag atgctgtata | 600 |
| gaggtgggat gcgaactcca aatgcacagc aaatagaaca gatcactgca cagctaggca | 660 |
| agtacggcaa gatcgaaggc aaaaacgttt tctattggtt ccaaaaccac aaagcacgcg | 720 |
| aaaggcaaaa gcagaagcgt aacagtcttg gtcttagcca ttctcccaga aactcagctc | 780 |
| ccattaccac tataactttg gacactaggg taagttcaaa ccaacaaaac cctttctgtg | 840 |
| tatatatata tataacggtt agttttagt ttttacttct tataaacaga gaaaattaac | 900 |
| aatgtttgtg tttatatata tagggggga agtaatggaa agagaggagg atagtccata | 960 |
| taagagaaag tgtaggagct ggtcttttga gtacttagaa gaagaaagca gatcatcatc | 1020 |
| gtcgagtcaa gaggaggaaa acagaactct ggagcttttc ccattgcacc cggaaggcag | 1080 |
| atcatgaagg gggtttcaac tttcaacttt caacttttca ctttcaaaat gaagggaaaa | 1140 |
| gggaagctta acccaaaacc aaaaagactg ctacaaaacc caaaactctg ttcccattta | 1200 |
| tgaaatgata aacttatgct ttgatgatcg atccatg | 1237 |

<210> SEQ ID NO 5
<211> LENGTH: 672
<212> TYPE: DNA
<213> ORGANISM: Corchorus capsularis

<400> SEQUENCE: 5

| | | |
|---|---|---|
| atgggaaaca tgaaggtgca tcagttggca cgtggcttat gggagcatga accctccctc | 60 |
| tcccttggtt gcaagcgctt acgccctctt gctcccaagc tccacccttc ctcttcccct | 120 |
| gatcatactt ccgtctcctc tttcgacctt aagaccttca ttcgtcccga agtggcccc | 180 |
| cggaaacttt gcccttctga cgacaagcga gattctcatt ctcgccaggt ggaaacgcac | 240 |
| ccagggggaa cgcggtggaa tccgacgcaa gagcagatag ggatactgga gatgctgtat | 300 |
| agaggtggga tgcgaactcc aaatgcacag caaatagaac agatcactgc acagctaggc | 360 |
| aagtacggca gatcgaaggc aaaaacgttt tctattggt tccaaaacca caaagcacgc | 420 |
| gaaaggcaaa agcagaagcg taacagtctt ggtcttagcc attctcccag aaactcagct | 480 |
| cccattacca ctataacttt ggacactagg ggggaagtaa tggaaagaga ggaggatagt | 540 |
| ccatataaga gaaagtgtag gagctggtct tttgagtact agaagaaga aagcagatca | 600 |
| tcatcgtcga gtcaagagga ggaaaacaga actctggagc ttttcccatt gcacccggaa | 660 |
| ggcagatcat ga | 672 |

<210> SEQ ID NO 6
<211> LENGTH: 223
<212> TYPE: PRT
<213> ORGANISM: Corchorus capsularis

<400> SEQUENCE: 6

Met Gly Asn Met Lys Val His Gln Leu Ala Arg Gly Leu Trp Glu His
1               5                   10                  15

Glu Pro Ser Leu Ser Leu Gly Cys Lys Arg Leu Arg Pro Leu Ala Pro
            20                  25                  30

Lys Leu His Pro Ser Ser Ser Pro Asp His Thr Ser Val Ser Ser Phe
        35                  40                  45

Asp Leu Lys Thr Phe Ile Arg Pro Glu Ser Gly Pro Arg Lys Leu Cys
    50                  55                  60

Pro Ser Asp Asp Lys Arg Asp Ser His Ser Arg Gln Val Glu Thr His

```
                65                  70                  75                  80
Pro Gly Gly Thr Arg Trp Asn Pro Thr Gln Glu Gln Ile Gly Ile Leu
                    85                  90                  95
Glu Met Leu Tyr Arg Gly Gly Met Arg Thr Pro Asn Ala Gln Gln Ile
                100                 105                 110
Glu Gln Ile Thr Ala Gln Leu Gly Lys Tyr Gly Lys Ile Glu Gly Lys
            115                 120                 125
Asn Val Phe Tyr Trp Phe Gln Asn His Lys Ala Arg Glu Arg Gln Lys
        130                 135                 140
Gln Lys Arg Asn Ser Leu Gly Leu Ser His Ser Pro Arg Asn Ser Ala
145                 150                 155                 160
Pro Ile Thr Thr Ile Thr Leu Asp Thr Arg Gly Glu Val Met Glu Arg
                165                 170                 175
Glu Glu Asp Ser Pro Tyr Lys Arg Lys Cys Arg Ser Trp Ser Phe Glu
                180                 185                 190
Tyr Leu Glu Glu Glu Ser Arg Ser Ser Ser Ser Gln Glu Glu Glu
            195                 200                 205
Asn Arg Thr Leu Glu Leu Phe Pro Leu His Pro Glu Gly Arg Ser
210                 215                 220
```

<210> SEQ ID NO 7
<211> LENGTH: 7
<212> TYPE: PRT
<213> ORGANISM: Unknown
<220> FEATURE:
<223> OTHER INFORMATION: Description of Unknown: WUSCHEL C-terminal
      domain peptide
<220> FEATURE:
<221> NAME/KEY: MOD_RES
<222> LOCATION: (1)..(1)
<223> OTHER INFORMATION: Glu or Arg

<400> SEQUENCE: 7

Xaa Thr Leu Pro Leu Phe Pro
1               5

<210> SEQ ID NO 8
<211> LENGTH: 7
<212> TYPE: PRT
<213> ORGANISM: Unknown
<220> FEATURE:
<223> OTHER INFORMATION: Description of Unknown: WUSCHEL C-terminal
      domain peptide
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (6)..(6)
<223> OTHER INFORMATION: Ser or Thr

<400> SEQUENCE: 8

Ala Xaa Leu Glu Leu Xaa Leu
1               5

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ccatgggaaa catgaaggtg c                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaaacgtcc atcatctgcc t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccatgggaaa catgaaggtg c                                              21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcatgatct gccttccggg                                                20
```

NUCLEOTIDE SEQUENCE ENCODING WUSCHEL-RELATED HOMEOBOX4 (WOX4) PROTEIN FROM *CORCHORUS OLITORIUS* AND *CORCHORUS CAPSULARIS* AND METHODS OF USE FOR SAME

RELATED APPLICATIONS

This application is a National Stage application of PCT/US2014/066599, filed Nov. 20, 2014, which claims the benefit of priority to U.S. Provisional Patent Application Ser. No. 61/907,617, filed Nov. 22, 2013.

SEQUENCE LISTING

The instant application contains a Sequence Listing which has been submitted via EFS-Web and is hereby incorporated by reference in its entirety. Said ASCII copy is named JGX_801_ST25.txt and is 11.6 kilobytes in size.

FIELD OF INVENTION

The present invention relates generally to the field of molecular biology and concerns a method for enhancing fiber yield-related traits by modulating expression in a plant of a nucleic acid encoding WUSCHEL-related homeobox4 protein (WOX4) polypeptide. More particularly, the present invention provides the WUSCHEL-related homeobox4 (WOX4) homologues isolated from two species of jute plants, namely, *C. olitorius* and *C. capsularis*, and its application in the production of bast fiber in the plant of jute, as well as a transgenic jute plant thereof.

BACKGROUND OF THE INVENTION

Jute is an eco-friendly and biodegradable natural fiber. It is a renewable resource with high biomass production per unit area of land. More than 100 jute species (including wild relatives) produce natural bast fiber. Jute is produced from plants in the genus *Corchorus*, which was once classified with the family Tiliaceae, more recently with Malvaceae. However, only two of these species, *C. olitorius* and *C. capsularis*, produce high quality fiber suitable for use in industrial purposes. Being a natural fiber, jute can be used in various ways, supplementing or replacing synthetics, and it has been receiving increasing attention from industry. As there is an increasing global demand for jute fiber, further improvement of jute fiber production is necessary. Thus, there is a significant interest in studying fiber biosynthesis and exploring the molecular biology involved in biosynthesis of this fiber.

Figure 1:
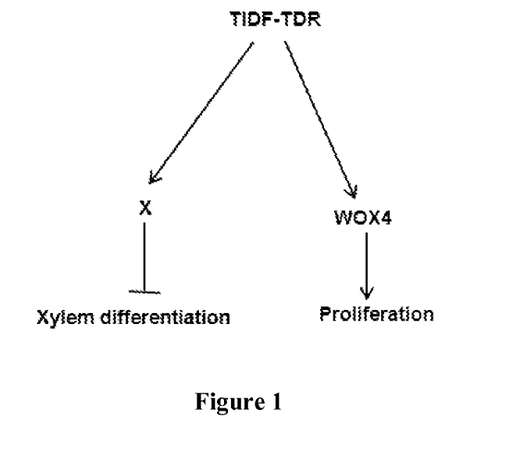
FIG. 1 displays TDIF-TDR signaling pathway. TDIF-TDR signaling diverges into two pathways, one is WOX4 involves in phloem cell proliferation, which promotes fiber cell initiation and another is a hypothetical factor X that inhibits xylem differentiation of vascular stem cells.
Figure 2:
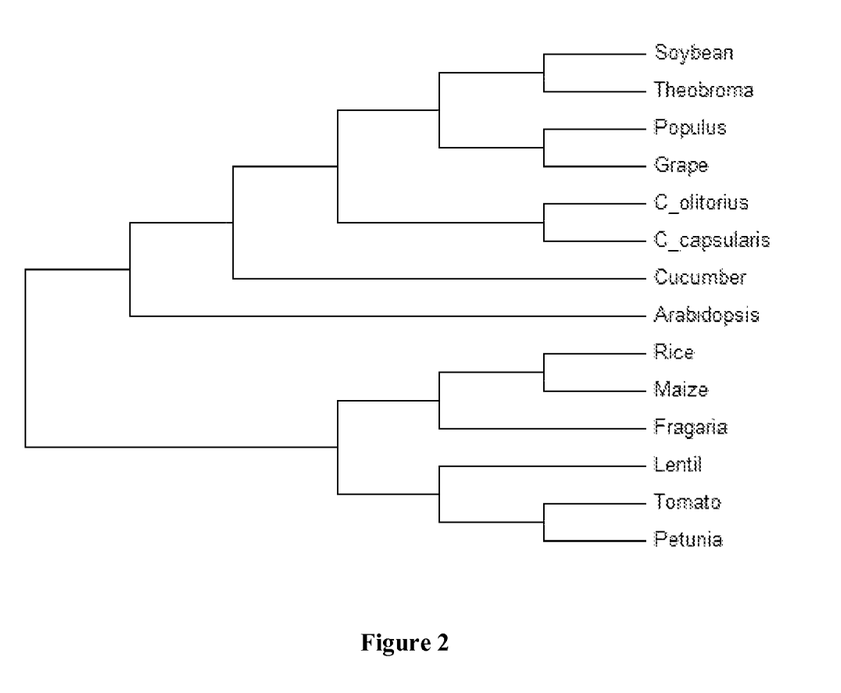
FIG. 2 displays the phylogenetic tree comparing SEQ ID NO. 3 from C. olitorius and SEQ ID NO. 6 from C. capsularis along with other amino acid sequences, which produce WUSCHEL-related homeobox4 (WOX4) protein.

Fiber of jute is an extraxylary fiber which is composed of and/or comprises two types of fiber: (i) primary phloem fiber that develops from procambium in the protophloem region through cell division and modification, and (ii) secondary phloem fiber that develops from cambium by the activity of fusiform and ray initials (Maiti and Mitra, 1972. Bull Bot Soc Bengal 26:79-85). These procambium and cambium tissues communicate cell-to-cell mediated by the tracheary element differentiation inhibitory factor (TIDF) and the TDIF receptor (TDR) membrane protein kinase, which promotes proliferation of procambial cells and suppresses their xylem differentiation (FIG. 1; Hirakawa et al., 2010. Plant Cell, 22:2618-2629; Etchells et al., 2013. Development 140, 2224-2234).

The WUSCHEL-related HOMEOBOX (WOX) gene family performs related functions during initiation and/or maintenance of various embryonic, meristematic, and organ initial cells (Haecker et al., 2004). Among the WUSCHEL-related HOMEOBOX (WOX) gene family proteins, WOX4 acts as a key regulator of TDIF signaling pathway (Hirakawa et al. 2010) and expressed preferentially in the procambium and cambium (Schrader et al., 2004; Ji et al., 2010 and Hirakawa et al. 2010). For example, TDIF-TDR induces the transcription of master transcription factor WUSCHEL-related HOMEOBOX4 (WOX4) that promotes the maintenance of procambium/cambium stem cells in *Arabidopsis* and in Tomato. WUSCHEL-related HOMEOBOX4 (WOX4) polypeptide catalyzes the initiation of bast fiber in plant. However, there are not many characterization reports or existing technologies provided in the prior art relating to this polypeptide. U.S. Patent No. 2011/0283420 A1 (incorporated by reference) has disclosed wuschel related homeobox 1-like (WOX1-like) polypeptide for enhanced yield-related traits in plants. In another E.P. Patent No. 1451301 B1 disclosed the use of wuschel gene in promotion of somatic embryogenesis in plants. Recently, some wuschel gene homologs were disclosed in U.S. Patent No. 2010/0100981 A1 (incorporated by reference).

In view of the fact that WUSCHEL-related homeobox4 protein could play an important role in the biosynthesis pathway of jute fiber, it is desirable for industry to provide a genetic approach relating to the biosynthesis of the fiber in the plant by exploring and utilizing the molecular biology and genetic information of WUSCHEL-related homeobox4 (WOX4). Besides, because the fiber biosynthesis pathway and genetic make-up of each species of plant typically varies, a species-specific approach is also preferable in order to optimize yield of fiber from jute plants, and obtain compatible results to enable use in industry.

SUMMARY OF THE INVENTION

One aspect of the present invention, amongst others, is to provide a gene encoding protein, derived from *C. olitorius* and *C. capsularis*, which is involved in catalyzing their initiation of bast fiber formation, and has a WUSCHEL-related homeobox4 (WOX4)-like sequence. More specifically, the present invention provides a gene that has the ability to induce phloem fiber, thus providing a protein encoded thereby, and uses thereof.

Another object of the present invention is to provide the molecular biology and genetic information of WUSCHEL-related homeobox4 (WOX4) to be exploited/utilized for improving the production, growth, strength and yield of fiber in the plants of *C. olitorius* and *C. capsularis*, as well as in other bast fiber-producing plants.

Still another object of the present invention is to obtain a transgenic plant of *C. olitorius* and *C. capsularis* with increased fiber production by regulating the biosynthesis of WUSCHEL-related homeobox4 (WOX4) in the plant.

Yet another object of the present invention is to provide isolated polynucleotides having specific nucleotide sequences, which may facilitate the performance of the disclosed method, and provide access to transgenic *C. olitorius* and *C. capsularis* plants.

Further object of the present invention is to provide a potential commercially feasible way to increase the production of fiber for jute fiber-based products.

The present invention provides a gene isolated from *C. olitorius* encoding a protein that has the amino acid sequence as set forth in SEQ ID NO: 3, which is involved in catalyzing the initiation of phloem fiber formation and has a WUSCHEL-related homeobox4 (WOX4)-like sequence.

The present invention further provides a gene encoding a protein that has an amino acid sequence modified by the addition or deletion of one or a plurality of amino acids and/or replacement with other amino acids in the amino acid sequence as set forth in SEQ ID NO: 3, which is involved in catalyzing the initiation of formation of phloem fiber and has a WUSCHEL-related homeobox4 (WOX4)-like sequence. The present invention further provides a gene that hybridizes to the nucleic acid as set forth in SEQ ID NO: 1, specifically its DNA or a portion thereof, and encodes a protein involved in catalyzing the initiation of formation of phloem fiber and has a WUSCHEL-related homeobox4 (WOX4)-like sequence.

The present invention also provides a gene isolated from C. capsularis encoding a protein that has the amino acid sequence as set forth in SEQ ID NO: 6, which is involved in catalyzing the initiation of formation of phloem fiber and has a WUSCHEL-related homeobox4 (WOX4)-like sequence. The present invention further provides a gene encoding a protein that has an amino acid sequence modified by the addition or deletion of one or a plurality of amino acids and/or replacement with other amino acids in the amino acid sequence as set forth in SEQ ID NO: 6, which is involved in catalyzing the initiation of formation of phloem fiber and has a WUSCHEL-related homeobox4 (WOX4)-like sequence. The present invention further provides a gene that hybridizes the nucleic acid as set forth in SEQ ID NO: 4, specifically its DNA or a portion thereof, and encodes a protein involved in catalyzing the initiation of formation of phloem fiber and has a WUSCHEL-related homeobox4 (WOX4)-like sequence.

According to one of the preferred embodiments of the present invention, the plant of C. olitorius used is variety O-4, and the plant of C. capsularis used is variety CVL-1. Another embodiment of the present invention discloses a recombinant gene construct comprising a polypeptide having nucleotide sequence set forth in SEQ ID NO: 2 and/or SEQ ID NO: 5, wherein the polynucleotide is expressible in a host cell to produce a homologue of WUSCHEL-related homeobox4 (WOX4) in the plant of C. olitorius and C. capsularis, respectively.

Further embodiment of the present invention is a transformant comprising a recombinant gene construct capable of expressing a polynucleotide having nucleotide sequence set forth in SEQ ID NO: 2 and/or SEQ ID NO: 5 to produce a homologue of WUSCHEL-related homeobox4 (WOX4) protein.

The present invention also provides a method for producing a protein involved in the catalytic activity for phloem fiber initiation, and has a WUSCHEL-related homeobox4 (WOX4)-like sequence, comprising culturing and/or cultivating the above host. The present invention also provides a method for inducing initiation of phloem fiber of plants or plant cells; furthermore, it also discloses a method comprising and/or consisting of introducing the above gene into plants or plant cells, and driving the expression of said genes.

One skilled in the art will readily appreciate that the present invention is well adapted to carry out the objects and obtain the ends and advantages mentioned, as well as those inherent therein. The embodiments described herein are not intended as limitations on the scope of the invention.

These and other features, aspects, and advantages of the present invention will be better understood with reference to the following description and claims.

DETAILED DESCRIPTION OF THE INVENTION

The invention can be more fully understood from the following detailed description and the accompanying drawings which form a part of this application.

The definitions and/or methods provided herein define the present invention and guide those of ordinary skill in the art in the practice of the present invention. Except where otherwise stated, terms are to be understood according to conventional usage by those of ordinary skill in the relevant art. To the extent to which any of the definitions and/or methods is found to be inconsistent with any of the definitions and/or methods provided in any patent or non-patent reference incorporated herein or in any reference found elsewhere, it is understood that the said definition and/or method which has been expressly provided/adopted in this application will be used herein. The singular terms "a," "an," and "the" include plural referents unless context clearly indicates otherwise. Similarly, the word "or" is intended to include "and" unless the context clearly indicates otherwise. Hence, "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

The present invention relates to isolated polynucleotides encoding WUSCHEL-related homeobox4 protein extracted from C. olitorius and C. capsularis, and corresponding polypeptides derived therefrom. More particularly, the present invention provides WUSCHEL-related homeobox4 homologues, and their application in enhanced fiber yield in C. olitorius and C. capsularis, both being species of jute plants, as well as related transgenic C. olitorius and C. capsularis plants. The genomic sequences of the invention encode the enzymes were identified primarily by comparison of nucleotide sequences of C. olitorius and C. capsularis genomic DNA and the nucleotide sequences of known enzyme genes of other plants. Prior to this invention, the nucleotide sequences of these C. olitorius and C. capsularis genes, the reading frames, the positions of exons and introns, the structure of the enzymes, and their potential usefulness in the development of high fiber yield potential jute plants were not known.

Analysis of the genome sequence of commercially cultivated jute species, C. olitorius and C. capsularis, reveals that both species have single genes coding for enzymes which possess preferred catalytic activities for enhancing fiber production. The nucleotide sequences were initially annotated by software programs, such as Augustus, Semi-HMM-based Nucleic Acid Parser (SNAP), Geneid (Genome BioInformatics Research Lab), which can identify putative coding regions, introns, and splice junctions. Further automated and manual curation of the nucleotide sequences was performed to refine and establish precise characterization of the coding regions and other gene features.

Over 30,096 cDNAs from *C. olitorius* and 37,031 cDNAs from *C. capsularis* were partially or fully sequenced. From them a single cDNA was developed from each of the species, encoding new enzymes, with putative roles, preferred catalytic activities in enhancing fiber production in jute.

Open reading frames (ORFs) are analyzed following full or partial sequencing of clones of cDNA libraries derived from *C. olitorius* and *C. capsularis* mRNA and are further analyzed using sequence analysis software, and by determining homology to known sequences in databases (public/private).

In the context of this disclosure, a number of terms used throughout the specification have the indicated meanings unless expressly indicated to have a different meaning.

As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may comprise and/or consist of one or more segments of cDNA, genomic DNA, synthetic DNA, or mixtures/combination thereof. An isolated polynucleotide of the present invention may include at least one of 150 contiguous nucleotides (both upstream and downstream) derived from SEQ ID No. 1 and, SEQ ID No. 4, or the complement of such sequences.

"Polypeptide" as used herein, is a single linear chain of amino acids bonded together by peptide bonds, and having usually a sequence greater than 100 amino acids in length.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

The term "gene", as used herein, is defined as the genomic sequences of the plant *C. olitorius* and *C. capsularis*, particularly polynucleotide sequence encoding polypeptide sequence of the WUSCHEL-related homeobox4 enzymes involved in the preferred catalytic activities in enhancing fiber production in jute. The term can further include nucleic acid molecules comprising upstream, downstream, and/or intron nucleotide sequences.

A "coding sequence" or "coding region" refers to a nucleic acid molecule having sequence information necessary to produce a gene product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The term "oligonucleotide" as used herein, is a short polynucleotide or a portion of polynucleotide, which may preferably comprise 10-1000, most preferably 12 to 50 nucleotides in length. In respect to the embodiment of the present invention, nucleotides contained within the oligonucleotides can be analogs or derivatives of naturally occurring nucleotides.

The term "primer" as used herein is an oligonucleotide capable of binding to a target nucleic acid sequence and priming the nucleic acid synthesis. An amplification oligonucleotide as defined herein may preferably be 10 to 50, most preferably 15 to 25, nucleotides in length. Furthermore, the amplification oligonucleotides of the present invention may be chemically synthesized and such oligonucleotides are not naturally occurring nucleic acids.

The abbreviation used throughout the specification to refer to nucleic acids comprising nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of the said hybridization depends upon detection method.

The term "host cell", as used herein, includes any cell type which is susceptible to transformation, transfection, transduction, expression and the like with a nucleic acid construct or expression vector comprising and/or consisting of a polynucleotide of the present invention. Suitable host cell includes fungi and/or plant cells, especially bast fiber producing plant cells.

The term "operably linked" generally denotes herein a configuration in which a control sequence is placed at an appropriate position relative to the coding sequence of the polynucleotide sequence such that the control sequence directs the expression of the coding sequence of a polypeptide. For example, a promoter can be operably-linked with a coding sequence when it affects the expression of that coding sequence, i.e., the coding sequence is under the transcriptional control of the promoter.

A "vector" generally refers to a replicon, such as plasmid, phage, cosmid, yeast or virus to which another nucleic acid segment may be operably inserted so as to bring about the replication or expression of the segment. The term "vector" is also intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene."

The term "promoter", as used herein, refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, "WUSCHEL polypeptide" or "WUS polypeptide" means a polypeptide having wuschel activity, i.e., involved in the initiation and maintenance of stem cells in plants. Wuschel activity stimulates cell growth, including stem cells. Wuschel is a plant homeodomain protein, comprising an 'atypical' (compared to the animal homeodomain motif) helix-loop-helix-turn-helix homeodomain motif comprising extra amino acid residues in the loop and/or turn of the domain. Wuschel proteins may further comprise and/or consist of other conserved motifs, such as the two conserved wuschel C-terminal domains, the (E/R)TLPLFP (SEQ ID NO: 7) and A(A/S)LEL(S/T)L (SEQ ID NO: 8) domains. The term is also inclusive of fragments, variants, and homologues, with any one of the above stated functions.

The term "homologues", as used herein, refers to a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues.

A substitution refers to replacement of amino adds of the protein with other amino acids having similar properties (such as similar hydrophobicity, hydrophilicity, antigenicity, propensity to form or break α-helical structures or β-sheet structures), Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions, Conservative substitution tables are well known in the art (see for example Creighton (1984) Proteins, W.H. Freeman and Company (Eds) and Table 1 below).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and/or any other synthetic techniques, or by recombinant DNA manipulation. Methods for, the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis or other site-directed mutagenesis protocols.

As used herein, a "biologically active portion" may refer to a fragment of WUSCHEL-related homeobox4 protein having a biological activity for catalyzing the initiation, formation, enhancement, or variation in the composition of phloem fiber in the plant of *C. olitorius* or *C. capsularis*. Biologically active portions of a WUSCHEL-related homeobox4 protein include peptides or polypeptides comprising amino acid sequences sufficiently identical to or derived from the amino acid sequence of the WUSCHEL-related homeobox4 protein, e.g., the amino acid sequence as set forth in SEQ ID NO: 3 or SEQ ID NO: 6, which include fewer amino acids than the full length WUSCHEL-related homeobox4 proteins, and exhibit at least one activity of a WUSCHEL-related homeobox4 protein. Typically, biologically active portions comprise a domain or motif with at least one activity of the WUSCHEL-related homeobox4 protein. A biologically active portion of a WUSCHEL-related homeobox4 protein can be a polypeptide which is, for example, 210, 211, 212, 213, 214, 215, 216, 217, 218, 219, 220, 221, 222, or 223 amino acids in length.

The WUSCHEL-related homeobox4 protein may have an amino acid sequence set forth in SEQ ID NO: 3 or SEQ ID NO: 6. In other embodiments, the WUSCHEL-related homeobox4 protein is substantially identical to SEQ ID NO: 3 or SEQ ID NO: 6, and retains the functional activity of the protein of SEQ ID NO: 3 or SEQ ID NO: 6, yet differs in amino acid sequence due to natural allelic variation or mutagenesis. In another embodiment, the WUSCHEL-related homeobox4 protein comprises an amino acid sequence at least about 95%, 96%, 97%, 98%, 99%, 99.1%, 99.2%, 99.3%, 99.4%, 99.5%, 99.6%, 99.7%, 99.8%, 99.9% or more identical to SEQ ID NO: 3 or SEQ ID NO: 6. The term "domain", as used herein, refers to a set of amino acids conserved at specific positions along an alignment of sequences of evolutionarily related proteins. While amino acids at other positions can vary between homologues, amino acids that are highly conserved at specific positions indicate amino acids which are likely to be essential in the structure, stability or function of a protein. Identified by their high degree of conservation in aligned sequences of a family of protein homologues, they can be used as identifiers to determine if any polypeptide in question belongs to a previously identified polypeptide family.

The term "motif", as used herein, refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: The Proteomics Server for In-depth Protein Knowledge and Analysis, Nucleic Acids Res. 31:3784-3788(2003)). Domains or motifs may also be identified using routine techniques, such as by sequence alignment.

For the purposes of the invention, "transgenic", "transgene" or "recombinant" means with regard to, for example, a nucleic acid sequence, an expression cassette, gene construct or a vector comprising and/or consisting of the nucleic acid sequence or an organism transformed with the nucleic acid sequences, expression cassettes or vectors according to the invention, all those constructions brought about by recombinant methods in which either: (a) the nucleic acid sequences encoding proteins useful in the methods of the invention, or (b) genetic control sequence(s) which is operably linked with the nucleic acid sequence according to the invention, for example a promoter, or (c) a) and b) are not located in their natural genetic environment or have been modified by recombinant methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of about 50 bp, preferably of about 500 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 (incorporated by reference) or WO 00/15815 (incorporated by reference).

A transgenic plant for the purposes of the invention is thus understood as including those plants in which the nucleic acids used in the method of the invention are not at their natural locus in the genome of the said plant, and thus it is possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, where homologous or, preferably, heterologous expression of the nucleic acids takes place.

The term "introduction" or "transformation", as used herein, encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained in non-integrated form, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation and chemicals which increase free DNA uptake, injection of the DNA directly into the plant, particle gun bombardment, transformation using viruses or pollen and microprojection. Transgenic plants, including transgenic crop plants, are preferably produced via Agrobacterium-mediated transformation. An advantageous transformation method is the transformation in planta (Sajib et. al. Plant Cell Tiss. Organ Cult. (2008) 95, 333-34).

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selected and homozygous second-generation (or T2) transformants may be selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "increased expression" or "overexpression" as used herein refers to any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a splice able intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Mol. Biol. 48:444-453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program, when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases.

A preferred alignment of selected sequences in order to determine "% identity" between two or more sequences is performed using, for example, the CLUSTAL-W program.

As in setting forth, one embodiment of the present invention are isolated polynucleotides encoding WUSCHEL-related homeobox4 polypeptide found in the plants C. olitorius and C. capsularis comprising and/or consisting of nucleotide sequence as set forth in SEQ ID NO 2 and SEQ ID NO 5, respectively. Correspondingly, the respective WUSCHEL-related homeobox4 polypeptides encoded by the nucleotide sequences possess the amino acid sequences set forth in SEQ ID NO 3 and SEQ ID NO 6. According to an embodiment of the present invention, SEQ ID NO 3 refers to the polypeptide sequence of the *C. olitorius*-derived WUSCHEL-related homeobox4 (WOX4) homologue, and SEQ ID NO 6 refers to the polypeptide sequence of the *C. capsularis*-derived WUSCHEL-related homeobox4 (WOX4) homologue. Both these enzymes are present in the biosynthesis pathway of fiber in the plants of *C. olitorius* and *C. capsularis* for catalyzing the initiator molecules for priming the biosynthesis of fiber cell in the plant.

The present invention also provides a gene sequence encoding the WUSCHEL-related homeobox4 (WOX4) homologues from the plants *C. olitorius* and *C. capsularis*.

In one embodiment, the 1250 bp long polynucleotide illustrated in SEQ ID No. 1 is the full length gene isolated from *C. olitorius*. This gene sequence includes at least 150 contiguous nucleotides from both upstream and downstream of the gene. This also provides the intronic sequence of the gene.

In another embodiment, the 1237 bp long polynucleotide illustrated in SEQ ID No. 4 is the full length gene isolated from *C. capsularis*. This gene sequence includes at least 150 contiguous nucleotides from both upstream and downstream of the gene. This also provides the intronic sequence of the gene.

In still another embodiment of the present invention, an isolated polynucleotide encoding a polypeptide comprising nucleotide sequence set forth in SEQ ID NO 2 and/or SEQ ID NO 5 is provided. SEQ ID NO 2 refers to the polynucleotide sequence of the *C. olitorius*-derived WUSCHEL-related homeobox4 (WOX4) homologue sequence and SEQ ID NO 5 refers to the polynucleotide sequence of the *C. capsularis*-derived WUSCHEL-related homeobox4 (WOX4) homologue sequence.

In still another embodiment, an isolated nucleic acid molecule which is capable of encoding a WUSCHEL-related homeobox4 polypeptide, or biologically active fragment thereof, comprises a nucleotide sequence which is at least about 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence set forth in SEQ ID NO: 2, SEQ ID NO: 5, or any complement thereof.

In one embodiment, the 669 bp long polynucleotide illustrated in SEQ ID No. 2 is the full length cDNA clone encoded WUSCHEL-related homeobox4 (WOX4) protein exhibiting an open reading frame encoding a 222 amino acid polypeptide, as in SEQ ID No. 3, with a calculated molecular mass of about 25.54 kD. Through SMART analysis of SEQ ID No. 3, it reveals presence of homeobox domain in the sequence. This is a DNA-binding factor, which is involved in the transcriptional regulation of key developmental processes of plant. This is WUSCHEL-related homeobox4 (WOX4) protein involved in the vascular cell proliferation of plant.

In one embodiment, the 672 bp long polynucleotide illustrated in SEQ ID No. 5 is the full length cDNA clone encoded WUSCHEL-related homeobox4 (WOX4) protein exhibiting an open reading frame encoding a 223 amino acid polypeptide, as in SEQ ID No. 6, with a calculated molecular mass of about 25.67 kD. Through SMART analysis of SEQ ID No. 6, it reveals presence of homeobox domain in the sequence. This is a DNA-binding factor, which is involved in the transcriptional regulation of key developmental processes of plant. This is WUSCHEL-related homeobox4 (WOX4) protein involved in the vascular cell proliferation of plant.

In accordance with the preferred embodiment of the present invention, the isolated polynucleotide illustrated in SEQ ID NO 2 can be obtained by PCR amplification of the conserved region of the gene using total RNA isolated from the plant of *C. olitorius* and SEQ ID NO 5 can be obtained by PCR amplification of the conserved region of this gene using total RNA isolated from the plant of *C. capsularis*. As set forth in the preceding description, the plant of *C. olitorius* applied is 0-4 variety and *C. capsularis* applied is CVL-1 variety.

Another embodiment of the present invention, a recombinant gene construct comprising a polynucleotide having nucleotide sequence set forth in SEQ ID NO 2 and/or SEQ ID NO 4 is disclosed, wherein the polynucleotide is expressible in a host cell, and is translable to produce homologue of WUSCHEL-related homeobox4 (WOX4) protein in the plants of *C. olitorius* and *C. capsularis*. The procedure for amplifying, cloning and sequencing the WUSCHEL-related homeobox4 (WOX4) from the plants of *C. olitorius* and *C. capsularis* is further detailed in Example 2. Preferably, the recombinant gene construct further comprises a promoter region operably-linked to enhance expression of the polynucleotide template. Under the transcriptional control of the specific promoter, the expression of the coding region within the recombinant gene constructs containing polynucleotide of SEQ ID NO 2 and/or SEQ ID NO 4 can then be enhanced, leading to higher yield of the WUSCHEL-related homeobox4 (WOX4) protein.

According to an embodiment of the invention, the modulated expression is increased expression or activity, e.g. over-expression of a WUSCHEL-related homeobox4 polypeptide encoding nucleic acid molecule, e.g., of a nucleic acid molecule encoding SEQ ID NO 2 and SEQ ID NO 5. Methods for increasing expression of nucleic acids or genes, or gene products, are well documented in the art and examples are provided in the definitions section.

The invention also provides a method for the production of transgenic plants having enhanced fiber yield relative to control plants, comprising introduction and expression in a plant of any nucleic acid encoding a WUSCHEL-related homeobox4 polypeptide as defined herein above.

More specifically, the present invention provides a method for the production of transgenic plants having enhanced fiber yield in comparison to the null control plants, which method comprises:
(i) introducing and expressing in a plant or plant cell a WUSCHEL-related homeobox4 polypeptide-encoding nucleic acid or a genetic construct comprising and/or consisting of a WUSCHEL-related homeobox4 polypeptide-encoding nucleic acid; and
(ii) cultivating the plant cell under conditions promoting fiber cell growth and development. Another aspect of the invention relates to isolated polynucleotide which encodes a WUSCHEL-related homeobox4 polypeptide, and is derived from the plant *C. olitorius*, comprising a nucleic acid molecule selected from the group consisting of:
a) a nucleic acid molecule comprising a nucleotide sequence set forth in of SEQ ID NO 2, or a complement thereof; and
b) a nucleic acid molecule comprising a nucleotide sequence having at least 95% sequence identity to the nucleotide sequence of set forth in SEQ ID NO: 2, or a complement thereof.

In certain embodiments, the plant of *C. olitorius* is variety O-4.

Another aspect of the invention relates to an isolated which encodes a WUSCHEL-related homeobox4 polypeptide and is derived from the plant *C. capsularis*, comprising a nucleic acid molecule selected from the group consisting of:
a) a nucleic acid molecule comprising a nucleotide sequence set forth in SEQ ID NO: 5, or a complement thereof; and
b) a nucleic acid molecule comprising a nucleotide sequence having at least 95% sequence identity to the nucleotide sequence set forth in SEQ ID NO: 5, or a complement thereof.

In certain embodiments, the plant of *C. capsularis* is variety CVL-1.

Another aspect of the invention relates to an isolated WUSCHEL-related homeobox4 polypeptide comprising an amino acid sequence set forth in SEQ ID: NO: 3, or biologically-active fragment thereof, said polypeptide comprises a function selected from the group consisting of catalyzing the initiation, formation, enhancement, and variation, to thereby modify the composition of phloem fiber in the plant of *C. olitorius*.

In certain embodiments, the plant of *C. olitorius* is variety O-4.

In certain embodiments, said polypeptide comprises at least 95% sequence identity to the amino acid sequence set forth in SEQ ID NO: 3.

Another aspect of the invention relates to an isolated WUSCHEL-related homeobox4 polypeptide comprising an amino acid sequence as set forth in SEQ ID NO: 6, or biologically-active fragment thereof, said polypeptide comprises one or more functions selected from the group consisting of catalyzing the initiation, formation, enhancement, and variation, to thereby modify the composition of phloem fiber in the plant of *C. capsularis*.

In certain embodiments, the plant of *C. capsularis* is variety CVL-1.

In certain embodiments, said polypeptide comprises at least 95% sequence identity to the amino acid sequence set forth in SEQ ID NO: 6.

Another aspect of the invention relates to a recombinant gene construct comprising a polynucleotide selected from the group consisting of:
a) a nucleic acid molecule comprising a nucleotide sequence set forth in SEQ ID NO: 2 or SEQ ID NO: 5, or a complement thereof; and
b) a nucleic acid molecule comprising a nucleotide sequence having at least 95% sequence identity to the nucleotide sequence set forth in SEQ ID NO: 2 or SEQ ID NO: 5, or a complement thereof, wherein the polynucleotide is expressible in a host cell to produce a homologue of WUSCHEL-related homeobox4 polypeptide in the plants of *C. olitorius* and *C. capsularis*.

In certain embodiments, said construct further comprises a promoter region operably-linked to
a) a nucleic acid molecule comprising a nucleotide sequence set forth in SEQ ID NO: 2 or SEQ ID NO: 5, or a complement thereof; or
b) a nucleic acid molecule comprising a nucleotide sequence having at least 95% sequence identity to the nucleotide sequence set forth in SEQ ID NO: 2 or SEQ ID NO: 5, or a complement thereof, wherein said promoter enhances the transcription or expression of the nucleic acid molecule.

Another aspect of the invention relates to a transformant comprising a recombinant gene construct capable of expressing a polynucleotide selected from the group consisting of:
a) a nucleic acid molecule comprising a nucleotide sequence set forth in SEQ ID NO: 2 or SEQ ID NO: 5, or a complement thereof; and
b) a nucleic acid molecule comprising a nucleotide sequence having at least 95% sequence identity to the nucleotide sequence set forth in SEQ ID NO: 2 or SEQ ID NO: 5, or a complement thereof, wherein said transformant produces a homologue of WUSCHEL-related homeobox4 polypeptide.

Another aspect of the invention relates to a method for producing a plant or transgenic plant having increased or enhanced fiber yield relative to control plants, comprising:
a) introducing into a plant cell a recombinant gent construct comprising a polynucleotide selected from the group consisting of: i) a nucleic acid molecule comprising a nucleotide sequence set forth in SEQ ID NO: 2 or SEQ ID NO: 5, or a complement thereof; and ii) a nucleic acid molecule comprising a nucleotide sequence having at least 95% sequence identity to the nucleotide sequence set forth in SEQ ID NO: 2 or SEQ ID NO: 5, or a complement thereof,
b) cultivating the plant cell under conditions for promoting plant growth and development; and
c) expressing a polypeptide selected from the group consisting of: i) a polypeptide comprising an amino acid sequence set forth in SEQ ID: NO: 3 or SEQ ID NO: 6, or a biologically-active fragment thereof; and ii) a polypeptide having at least 95% sequence identity to the amino acid sequence set forth in SEQ ID NO: 3 or SEQ ID NO: 6.

The sequences provided by the present invention can also be used as preparatory materials for the rational modification or design of novel enzymes with characteristics that enable the enzymes to perform better in demanding processes.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention and claims.

Various references are cited herein, the disclosures of which are incorporated by reference in their entireties.

EXAMPLES

The following examples are intended to further illustrate the invention, without any intent for the invention to be limited to the specific embodiments described therein.

Example 1 Designing and Synthesis of Primers

The primers used in the study were either designed from the manually curated transcriptome and the "gene models" predicted from the genomic sequences of *C. olitorius* and *C. capsularis*, by choosing the sequences manually with complete ORFs or using databases where similar genes have been successfully isolated from other plants. Comparative bioinformatic analysis of the nucleotide sequences obtained from transcriptome were carried out using NCBI BLAST, BLASTP, RPS-BLAST, BLASTX and PSI-BLAST to identify homologues of the related genes and for the proper identification of gene. Nucleotide sequence alignments were performed through clustalW version 1.82 whenever multiple sequences were found from the "gene pool". The alignment was then edited. Gene specific primers (both forward and reverse) were selected manually or through Primer 3 plus tool and the primers were custom synthesized.

All oligonucleotides used in this study were synthesized and HPLC purified by the supplier and procured from Integrated DNA Technologies (IDT). Stock solution of about 100 pmol were prepared in autoclaved ddH₂O and stored at about −20° C., in aliquots for use.

Oligonucleotides Sequences used as primers for PCR

| Primer name | SEQ ID NO | Oligonucleotide sequence | Amplified product from cDNA |
|---|---|---|---|
| COL F | 1 | CCATGGGAAACATGAAGGTGC (SEQ ID NO: 9) | 682 |
| COL R | 1 | TGAAACGTCCATCATCTGCCT (SEQ ID NO: 10) | |
| CCA F | 4 | CCATGGGAAACATGAAGGTGC (SEQ ID NO: 11) | 675 |
| CCA R | 4 | TTCATGATCTGCCTTCCGGG (SEQ ID NO: 12) | |

Example 2 Amplification, Cloning and Sequencing of WUSCHEL-Related Homeobox4 from *C. Olitorius* and *C. Capsularis*

Total RNA was isolated from three days old seedlings grown on MS medium as previously described by Chomezynski P and Sacehi N, Single-step method of RNA isolation by acid guanidinium thiocyanate-phenol-chloroform extraction. (Anal Biochem 1987, 162: 156-159). The quality or the integrity of the RNA was checked by agarose gel electrophoresis and was quantified using Thermo Scientific Nano Drop 2000 as per standard procedures. cDNA first strand was synthesised using SuperScript III reverse transcriptase (Invitrogen) following the manufacturer's instructions. The gene was amplified from the cDNA by PCR using the gene specific primers. The PCR reaction (50 µL) contained 1 µL of cDNA, 20 pmoles of each primers, 5 µL of 10×PCR Buffer, 5 µL of 2.5 mM dNTP mix and 1.0 unit of PfuTaq DNA polymerase. PCR was carried out in Thermal Cycler (Applied Biosystems) using the following conditions: initial denaturation for about 5 min at approximately 95° C. followed by 35 cycles of denaturation at approximately 95° C. for about 30 sec, annealing at approximately 59-61° C. for about 30 sec and extension at approximately 72° C. for about 1 min, with a final extension at approximately 72° C. for about 7 min. The PCR product was analyzed by 1% agarose gel using 1×TAE buffer and the amplicon was eluted from the gel using QIAGEN gel extraction kit following the manufacturer's instructions. The purified PCR product was ligated into pCR®8/GW/TOPO® TA cloning kit (Invitrogen) and transformed into competent *E. coli* cells (Invitrogen). Plasmids were isolated from putative colonies using QIAprip Spin Miniprep Kit (QIAGEN) following the manufacturer's instructions. The presence of the insert was checked by using the gene specific primers and positive plasmids were subjected to Sequencing.

Example 3 Analysis of the Sequence

The nucleotide sequence and the amino acid sequence were analyzed by BLASTN and BLASTP programs respectively. The sequences reported from other plants were aligned with ClustalW. Phylogenetic analysis was carried out using the Neighbour Joining (NJ).

Example 4 Pathway Construction of Fiber Biosynthesis

Automatic metabolic pathway reconstruction showcasing role of WUSCHEL-related homeobox4 (WOX4) in fiber biosynthesis was constructed by identifying orthologs from *C. olitorus* and *C. capsularis* protein compared with *Arbidopsis* genome. WUSCHEL-related homeobox4 (WOX4) catalyzed enzymatic reactions encoded within *C. olitorus* and *C. capsularis* genome were constructed using enzymatic reactions available in Resnet-Plant 3.0 database for Pathway Studio as well as from metabolic pathway databases.

INCORPORATION BY REFERENCE

All of the U.S. patents, U.S. published patent applications, and published PCT applications that cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practised otherwise than as specifically described and claimed.

SEQ ID NO: 1
LENGTH: 1250 bp
TYPE: DNA
FEATURE NAME/KEY: Intron, exon including 150 bp 5' UTR and 150 bp 3' UTR
ORGANISM: Jute, C. olitorius (SEQ ID NO: 1)

ACCTCATCATTTGGTCTTGGTTCTTCAAAGCACCACCTCATATCCCACTTTCTTTTTCTTTTCTTTT

TTTTAAAATTTTTATTTTTTGGGTTAAATTTATTTTTGTTATTATATAATCAGAGCATTCTCCCCAT

CATTCACTCCTTCACCATGGGAAACATGAAGGTGCATCAGTTGGCACGTGGCTTATGGGAGCATGAA

CCCTCCCTCTCCCTTGGTTGCAAGCGCTTACGCCCTCTTGCTCCCAAGCTCCACCCTTCCTCTTCCC

CTGATCATACTTCCGTCTCCTCTTTCGACCTTAAGACCTTCATTCGTCCCGAAAGTGGCCCCCGAAA

-continued

ACTTTGCCCTTCTGACGACAAGCGAGATTCTCATTCTCCCCAGGTACTTACAAATATCCATGAAATG

AAACCCTTTTATTTTTCCAATGATGTATATAATTAGTGGGGAAGGATAAGATTTTGAACTTACGATG

AACAATAACAGTGTGGAAAGTTGATAATCAAAGGTTAAGAATGTGAAGCTGAAACTTTTTTCTTTTT

TTTGGTTATGTAGGTGGAAACGCACCCAGGGGGAACGCGGTGGAATCCGACGCAAGAGCAGATAGGG

ATATTGGAGATGCTGTATAGAGGTGGGATGCGAACTCCAAATGCACAGCAAATAGAACAGATCACTG

CACAGTTAGGCAAGTACGGGAAGATCGAAGGCAAAAACGTTTTCTATTGGTTCCAAAACCACAAAGC

ACGCGAAAGGCAAAAGCAGAAGCGTAACAGTCTTGGTCTTAGCCATTCTCCCAGAAACTCTGCTCCC

ATTACCACCATAACTTTGGACTCTAGGGTAAGTTCAAACCAACAAAACCCTTTCTTTGTATATATAT

AACGGTTAGTTTTTAGTTTTTACTTCTTATAAACAGCAATTAACATTAATGTTTTGTTTATATATA

TAGGGGGAAGTAATGGAGAGAGAGGAGGATAGTCCATATAAGAGAAAGTGTAGGAGCTGGTCATTTG

AGTACTTAGAAGAAGAAAGCAGATCATCATCGTCGAGTCAAGAGGAGGAAAACAGAACTCTGGAGCT

TTTCCCATTGCACCCGGAAGGCAGATGATGGACGTTTCAACTTTGAAAAACAAGGAAAAAGGGAAGC

TTAACCCAAAACCAAAAGACTGCTACAAAACCCAAAACTCTGTTCCCATTTATGAAATGATAAACA

TATGCTTTGATGATCCATGATGATGATGATGATAATGAAGCTGA

SEQ ID NO: 2
LENGTH: 669 bp
TYPE: DNA
ORGANISM: Jute, C. olitorius
FEATURE NAME/KEY: CDS
LOCATION: (1) ... (669)

(SEQ ID NO: 2)

ATGGGAAACATGAAGGTGCATCAGTTGGCACGTGGCTTATGGGAGCATGAACC

CTCCCTCTCCCTTGGTTGCAAGCGCTTACGCCCTCTTGCTCCCAAGCTCCACCCT

TCCTCTTCCCCTGATCATACTTCCGTCTCCTCTTTCGACCTTAAGACCTTCATTCG

TCCCGAAAGTGGCCCCCGAAAACTTTGCCCTTCTGACGACAAGCGAGATTCTCA

TTCTCCCCAGGTGGAAACGCACCCAGGGGAACGCGGTGGAATCCGACGCAAG

AGCAGATAGGGATATTGGAGATGCTGTATAGAGGTGGGATGCGAACTCCAAAT

GCACAGCAAATAGAACAGATCACTGCACAGTTAGGCAAGTACGGGAAGATCGA

AGGCAAAAACGTTTTCTATTGGTTCCAAAACCACAAAGCACGCGAAAGGCAAA

AGCAGAAGCGTAACAGTCTTGGTCTTAGCCATTCTCCCAGAAACTCTGCTCCCA

TTACCACCATAACTTTGGACTCTAGGGGGAAGTAATGGAGAGAGAGGAGGAT

AGTCCATATAAGAGAAAGTGTAGGAGCTGGTCATTTGAGTACTTAGAAGAAGA

AAGCAGATCATCATCGTCGAGTCAAGAGGAGGAAAACAGAACTCTGGAGCTTT

TCCCATTGCACCCGGAAGGCAGATGA

SEQ ID NO: 3
LENGTH: 222
TYPE: PRT
ORGANISM: Jute, C. olitorius (SEQ ID NO: 3)

MGNMKVHQLARGLWEHEPSLSLGCKRLRPLAPKLHPSSSPDHTSVSSFDLKTFIRPESGPRKLCPSD

DKRDSHSPQVETHPGGTRWNPTQEQIGILEMLYRGGMRTPNAQQIEQITAQLGKYGKIEGKNVFYWF

QNHKARERQKQKRNSLGLSHSPRNSAPITTITLDSRGEVMEREEDSPYKRKCRSWSFEYLEEESRSS

SSSQEEENRTLELFPLHPEGR*

SEQ ID NO: 4
LENGTH: 1237 bp
TYPE: DNA
FEATURE NAME/KEY: Intron, exon including 150 bp 5' UTR and 150 bp 3' UTR
ORGANISM: Jute, C. capsularis -continued (SEQ ID NO: 4)
TCACAAGTCAACCTCACCTCATCATTTGGTCTTGGTTCTTCAAAGCACCACCTCATATCCCACTTCC

TTTTTCAATTTTTAATTTTTTTGGGGTTAAATTTATTTGGTTATATAATCAGAGCATTCTCCCCAT

CATTCACTCCTTCACCATGGGAAACATGAAGGTGCATCAGTTGGCACGTGGCTTATGGGAGCATGAA

CCCTCCCTCTCCCTTGGTTGCAAGCGCTTACGCCCTCTTGCTCCCAAGCTCCACCCTTCCTCTTCCC

CTGATCATACTTCCGTCTCCTCTTTCGACCTTAAGACCTTCATTCGTCCCGAAAGTGGCCCCCGGAA

ACTTTGCCCTTCTGACGACAAGCGAGATTCTCATTCTCGCCAGGTACTTAAAAATTAATATCCATGA

AATAATTTGTGGGGAAGGATAAGTTTTGAACTTAATGCATAATAACAGTGTGGAAACTTAATAGGTT

AAGAATATTTGAAGAACTTCTATATATATGAAGCTGAAACTTTTTTGTGGTGTTGTAGGTGGAAACG

CACCCAGGGGGAACGCGGTGGAATCCGACGCAAGAGCAGATAGGGATACTGGAGATGCTGTATAGAG

GTGGGATGCGAACTCCAAATGCACAGCAAATAGAACAGATCACTGCACAGCTAGGCAAGTACGGCAA

GATCGAAGGCAAAAACGTTTTCTATTGGTTCCAAAACCACAAAGCACGCGAAAGGCAAAAGCAGAAG

CGTAACAGTCTTGGTCTTAGCCATTCTCCCAGAAACTCAGCTCCCATTACCACTATAACTTTGGACA

CTAGGGTAAGTTCAAACCAACAAAACCCTTTCTGTGTATATATATATATAACGGTTAGTTTTTAGTT

TTTACTTCTTATAAACAGAGAAAATTAACAATGTTTGTGTTTATATATATAGGGGGAAGTAATGG

AAAGAGAGGAGGATAGTCCATATAAGAGAAAGTGTAGGAGCTGGTCTTTTGAGTACTTAGAAGAAGA

AAGCAGATCATCATCGTCGAGTCAAGAGGAGGAAAACAGAACTCTGGAGCTTTTCCCATTGCACCCG

GAAGGCAGATCATGAAGGGGGTTTCAACTTTCAACTTTCAACTTTCAAAATGAAGGGAAA

AGGGAAGCTTAACCCAAACCAAAAGACTGCTACAAAACCCAAAACTCTGTTCCCATTTATGAAAT

GATAAACTTATGCTTTGATGATCGATCCATG

SEQ ID NO: 5
LENGTH: 672
TYPE: DNA
ORGANISM: Jute, C. capsularis
FEATURE NAME/KEY: CDS
LOCATION: (1) ... (672)

(SEQ ID NO: 5)
ATGGGAAACATGAAGGTGCATCAGTTGGCACGTGGCTTATGGGAGCATGAACCCTCCCTCTCCCTTG

GTTGCAAGCGCTTACGCCCTCTTGCTCCCAAGCTCCACCCTTCCTCTTCCCCTGATCATACTTCCGT

CTCCTCTTTCGACCTTAAGACCTTCATTCGTCCCGAAAGTGGCCCCCGGAAACTTTGCCCTTCTGAC

GACAAGCGAGATTCTCATTCTCGCCAGGTGGAAACGCACCCAGGGGAACGCGGTGGAATCCGACGC

AAGAGCAGATAGGGATACTGGAGATGCTGTATAGAGGTGGGATGCGAACTCCAAATGCACAGCAAAT

AGAACAGATCACTGCACAGCTAGGCAAGTACGGCAAGATCGAAGGCAAAAACGTTTTCTATTGGTTC

CAAAACCACAAAGCACGCGAAAGGCAAAAGCAGAAGCGTAACAGTCTTGGTCTTAGCCATTCTCCCA

GAAACTCAGCTCCCATTACCACTATAACTTTGGACACTAGGGGGAAGTAATGGAAAGAGAGGAGGA

TAGTCCATATAAGAGAAAGTGTAGGAGCTGGTCTTTTGAGTACTTAGAAGAAGAAAGCAGATCATCA

TCGTCGAGTCAAGAGGAGGAAAACAGAACTCTGGAGCTTTTCCCATTGCACCCGGAAGGCAGATCAT

GA

SEQ ID NO: 6
LENGTH: 223
TYPE: PRT
ORGANISM: Jute, C. capsularis (SEQ ID NO: 6)
MGNMKVHQLARGLWEHEPSLSLGCKRLRPLAPKLHPSSSPDHTSVSSFDLKTFIRPESGPRKLCPSD

DKRDSHSRQVETHPGGTRWNPTQEQIGILEMLYRGGMRTPNAQQIEQITAQLGKYGKIEGKNVFYWF

QNHKARERQKQKRNSLGLSHSPRNSAPITTITLDTRGEVMEREEDSPYKRKCRSWSFEYLEEESRSS

SSSQEEENRTLELFPLHPEGRS*

What is claimed is:

1. An isolated polynucleotide comprising a cDNA having at least 98% sequence identity to the nucleotide sequence set forth in SEQ ID NO: 2 or 5, wherein said polynucleotide encodes a WUSCHEL-related homeobox4 (WOX4) polypeptide.

2. A recombinant gene construct comprising the isolated polynucleotide of claim 1.

3. The recombinant gene construct according to claim 2, further comprising a promoter region operably-linked to the isolated polynucleotide of claim 1, wherein said promoter enhances the transcription or expression of the polynucleotide.

4. A transformant comprising the recombinant gene construct of claim 2.

5. A method for producing a transgenic plant cell, the method comprising the steps of:
   a) introducing into a plant cell the recombinant gene construct of claim 2;
   b) expressing a polypeptide having at least 95% sequence identity to the amino acid sequence set forth in SEQ ID NO: 3 or SEQ ID NO: 6, wherein said polypeptide has WOX4 activity; and
   c) cultivating the plant cell under conditions for promoting plant growth and development.

6. An expression construct comprising the isolated polynucleotide of claim 1, wherein the polynucleotide is operatively associated with a regulatory nucleotide sequence containing transcriptional or translational regulatory signals, or both, that controls expression of the polynucleotide in a host cell.

7. A material derived from the transformant of claim 4, wherein said material comprises the polynucleotide encoding the WOX4 polypeptide.

8. A seed from the transformant of claim 4, wherein said seed comprises the polynucleotide encoding the WOX4 polypeptide.

9. A method of inducing, initiating, improving, or enhancing plant growth, plant height, fiber and seed yield in a jute plant, comprising incorporating in to a jute plant the expression construct of claim 6.

10. The expression construct of claim 6, wherein said cDNA has at least 99% sequence identity to said nucleotide sequence.

11. The expression construct of claim 6, wherein said cDNA has 100% sequence identity to said nucleotide sequence.

12. The isolated polynucleotide of claim 1, wherein said cDNA has at least 99% sequence identity to said nucleotide sequence.

13. The isolated polynucleotide of claim 1, wherein said cDNA has 100% sequence identity to said nucleotide sequence.

* * * * *